US008958064B2

(12) United States Patent
Wiemer et al.

(10) Patent No.: US 8,958,064 B2
(45) Date of Patent: Feb. 17, 2015

(54) INSPECTION DEVICE WITH ROTATABLE LIGHTING ELEMENT HOUSING

(75) Inventors: Heinrich Wiemer, Hamburg (DE); Horst Böcker, Schwerte (DE)

(73) Assignee: KHS GmbH, Dortmund (DE)

( * ) Notice: Subject to any disclaimer, the term of this patent is extended or adjusted under 35 U.S.C. 154(b) by 1329 days.

(21) Appl. No.: 12/863,583

(22) PCT Filed: Aug. 27, 2008

(86) PCT No.: PCT/EP2008/006997
§ 371 (c)(1),
(2), (4) Date: Dec. 29, 2010

(87) PCT Pub. No.: WO2009/056188
PCT Pub. Date: May 7, 2009

(65) Prior Publication Data
US 2011/0102782 A1 May 5, 2011

(30) Foreign Application Priority Data

Oct. 31, 2007 (DE) .......................... 10 2007 052 302

(51) Int. Cl.
*G01N 21/15* (2006.01)
*G01N 21/90* (2006.01)
*G01N 21/21* (2006.01)

(52) U.S. Cl.
CPC ............ *G01N 21/15* (2013.01); *G01N 21/9009* (2013.01); *G01N 21/21* (2013.01); *G01N 2021/151* (2013.01); *G01N 2021/152* (2013.01); *G01N 2201/0634* (2013.01)

USPC ................... 356/239.4; 356/445; 356/239.1

(58) Field of Classification Search
CPC ........ G01N 21/15; G01N 21/21; G01N 21/90
USPC ..................... 356/445, 239.1–239.6
See application file for complete search history.

(56) References Cited

U.S. PATENT DOCUMENTS

| 5,926,268 | A | * | 7/1999 | Bonewitz et al. .......... 356/240.1 |
| 6,012,344 | A | | 1/2000 | Halbo |
| 2004/0194605 | A1 | | 10/2004 | Weber |
| 2004/0263838 | A1 | * | 12/2004 | Diehr .......................... 356/239.1 |
| 2005/0183393 | A1 | | 8/2005 | Engesser et al. |

FOREIGN PATENT DOCUMENTS

| DE | 38 39 682 A1 | 6/1989 |
| DE | 196 05 133 A1 | 8/1997 |

(Continued)

*Primary Examiner* — Kara E Geisel
*Assistant Examiner* — Iyabo S Alli
(74) *Attorney, Agent, or Firm* — Occhiuti & Rohlicek LLP

(57) ABSTRACT

The invention relates to an inspection device for monitoring containers, particularly bottles, comprising at least one transport path for supplying and removing the containers, a lighting unit, and optical measuring unit, and a control unit, wherein the lighting unit is surrounded by a transparent hollow body mounted in a rotatable fashion about the central axis, and the hollow body may be driven by a motor, either directly or via appropriate operative connections. Ideally, the hollow body is a tube made of a material or mixture of materials that is transparent to rays in the optically visible wavelength range, in the infrared range, and/or in the ultraviolet range, wherein the material is at least partially transparent to said rays.

20 Claims, 3 Drawing Sheets

(56) References Cited

FOREIGN PATENT DOCUMENTS

| | | |
|---|---|---|
| DE | 29617228 | 12/1997 |
| DE | 20004954 | 2/2002 |
| DE | 101 47 617 A1 | 4/2003 |
| DE | 202004010515 | 10/2004 |
| EP | 1 600 762 A | 11/2005 |
| FR | 2 768 517 A | 3/1999 |
| WO | 2007/039074 | 4/2007 |

* cited by examiner

INSPECTION DEVICE WITH ROTATABLE LIGHTING ELEMENT HOUSING

CROSS-REFERENCE TO RELATED APPLICATIONS

This application is the National Stage of International Application No. PCT/EP2008/006997, filed on Aug. 27, 2008, which claims the benefit of Germany Application Serial No. 10-2007 052 302.7, filed on Oct. 31, 2007, the contents of both of the foregoing applications are hereby incorporated by reference in their entirety.

FIELD OF INVENTION

The invention relates to an inspection device for checking containers, in particular bottles.

BACKGROUND

Devices for illuminating and inspecting container bottoms are known and adequately described in the prior art. EP 0 894 544 A discloses an inspection machine in which the containers, in this case bottles, are conveyed in a suspended manner above an illuminating device. The illuminating device itself is a cuboid-shaped block that shines through the bottles from below. In principle, these devices are proven and suitable. But they have to be cleaned relatively frequently in order to ensure reliable operation and meaningful measured values.

DE 10 2005 057 872 A1 proposes producing the conveyor, which is illuminated from below and on which the bottles to be inspected stand, so as to be transparent and in the form of a turntable. This reduces the contamination on the illuminating unit itself. But solid and liquid adhesions on the transparent turntable itself also require regular cleaning.

SUMMARY

It is an object of the invention to make available a device that reduces the amount of time and money spent on cleaning.

This object is achieved by an inspection device for checking containers, in particular bottles. The inspection device includes at least one conveying section for supplying and removing the containers, an illuminating unit, an optical measuring unit and a control unit. The conveying section can be one or more conveyor belts, conveying stars or a combination of conveyor belts and stars. The core of the inspection device is the illuminating device, which is surrounded by a transparent hollow body that is mounted so as to be rotatable about the central axis, the hollow body being drivable in a motor-driven manner directly or by means of suitable operative connections. Dirt, label residue, dust and moisture can be removed from the monitoring region in this manner without interrupting the actual measuring or monitoring processes. The axis of rotation of the hollow body, in principle, can be aligned in an arbitrary manner. In one embodiment, the axis of rotation of the hollow body is aligned parallel or transversely relative to the conveying direction of the containers.

In one aspect, the invention features an inspection device including at least one conveying section for supplying or removing the containers, an illuminating unit, an optical measuring unit and a control unit, wherein the illuminating unit is surrounded by a transparent hollow body that is mounted so as to be rotatable about the central axis and the hollow body is driveable in a motor-driven manner directly or by means of suitable operative connections. In an ideal manner, the hollow body is a tube produced from a material or a material mixture that is transparent to rays of wavelengths in the optically-visible range, in the infrared range, and/or in the ultraviolet range, wherein the material is at least partially transparent to these rays.

In some embodiments, the hollow body is a tube produced from a material or a material mixture that is at least partially transparent to rays of wavelengths in the optically-visible range, in the infrared range and/or in the ultraviolet range. In principle, known materials, such as PTFE, acrylic glass or tempered glass, can be used for this purpose.

In other embodiments, the inspection device has a diffusion element is located between the hollow body and the top side of the illuminating unit. The diffusion element results in the illuminating means being homogenized. In this case, the term "top side" of the illuminating device refers to the side that points to the container to be inspected or to the bottle to be inspected and by means of which the light is emitted. The corresponding counterpart is referred to as the bottom side.

In principle, the diffusion element can have a planar, level form. However, it has been shown that, an arc-shaped diffusion element is advantageous. Such a diffusion element is located between hollow body and the top side of the illuminating unit.

A further improvement of the inspection device can be achieved when a polarization filter is provided, for example, between the hollow body and the top side of the illuminating unit. Preferably, the polarization filter is arc-shaped. The use of polarization filters, or circular polarization filters, for inspection machines is known and is used, for example, to reliably detect transparent solids, such as films, in the container.

Suitable polarization filters are produced, for example, by a polyvinyl alcohol film that can be stabilized mechanically by a two-sided coating of cellulose acetobutyrate. Additional materials are known in principle and can be used depending on the application.

In some embodiments, a cleaning unit is located on the hollow body of the inspection device, said cleaning unit, preferably below the illuminating unit. The cleaning unit can also include a feeding device having outlets or nozzles for supplying the outside surface of the hollow body. These are suitable for gaseous or liquid media.

In another embodiment, the cleaning unit includes at least one removing device that has mechanical scrapers in the form of brushes, sealing lips made of a resilient material or suction elements. These remove solid or liquid adhesions from the surface of the hollow body. Through the rotation of the hollow body, the adhesions are conveyed in a permanent or sequential manner from the top side, that is, from the inspection field, to the bottom side. Any suitable, necessary wet and/or dry cleaning process can be effected at this location without having to consider the measuring and inspection device.

The rotating hollow body of the inspection device can be open at least at one side for reasons of heat development or for the supplying of power. In this way, deposits can pass onto the inside surface and be conducted into the inspection field. In one preferred embodiment, the cleaning unit extends onto or into the hollow body in such a manner that at least solid or liquid adhesions can be removed from the outside surface of the hollow body. Preferably, these are also removable from the inside surface. In the case of a cylindrical hollow body, a cantilever arm that includes the suitable scraper can extend into the interior and there carry out the cleaning work.

In an alternative embodiment, the hollow body is closed and connected to a gas line, by means of which, in normal operation an inert gas, or compressed air, can be directed into the interior of the hollow body. By maintaining a permanent over-pressure in the interior of the hollow body, contamination of the inside surfaces can be reliably avoided.

In addition, the invention also includes a method for inspecting containers, in particular bottles, where an inspection device according to one of the preceding embodiments is used.

The essential method steps are continuously or occasionally rotating the hollow body, supplying containers, suspended transport thereof in the region of the inspection unit, inspection of the containers, and removal of the containers.

In some practices of the method, the surface of the hollow body is cleaned permanently or at intervals by having a gas, ideally filtered compressed air, permanently directed into the hollow body. In the interior of the hollow body, the pressure maintained is preferably greater than the ambient pressure. Preferably, the pressure exceeds the ambient pressure by 0.2 to 0.5 bars. The gas or the compressed air, which can be referred to as flushing gas, has a dual function, namely to keep the interior free of contamination, and to cool the interior. Consequently, it can be advantageous for a cooling device to be located in the line path of the gas supply line, by means of which cooling device the gas can be cooled, at least sometimes. In addition, it can be advantageous to dry the flushing gas prior to introducing it into the hollow body.

In one aspect, the invention features an inspection device for checking containers. Such an inspection device includes a conveying section or conveying star for supplying and removing the containers, an illuminating unit, an optical measuring unit, and a control unit. A transparent hollow body that is mounted so as to be rotatable about the central axis surrounds the illuminating unit. The hollow body is drivable in a motor-driven manner directly or by suitable operative connections. An axis of rotation of the hollow body is aligned parallel or transversely relative to a conveying direction of the containers.

In some embodiments, the hollow body comprises a tube produced from a material or a material mixture, the material or material mixture being transparent to rays of wavelengths in the optically-visible range, in the infrared range and/or in the ultraviolet range, and wherein the material or material mixture is at least partially transparent to those rays.

Other embodiments include a diffusion element located between the hollow body and a top side of the illuminating unit. Among these are embodiments in which the diffusion element is arc-shaped and located between the hollow body and the top side of the illuminating unit, those in which a polarization filter is located between the hollow body and a top side of the illuminating unit, those in which this polarization filter is arc-shaped and located between the hollow body and a top side of the illuminating unit, and those in which this polarization filter is located between the hollow body and the diffusion element. Since the order of polarization filter and diffusion element does not matter, there are also embodiments in which the sequence of polarization filter and diffusion element is inverted so that it is the diffusion element that is between the hollow body and the polarization filter.

Other embodiments include a cleaning unit located on the hollow body. Among these are embodiments in which the cleaning unit has a feeding device, with the feeding device having outlets or nozzles for illuminating an outside surface of the hollow body, wherein the feeding device is suitable for gaseous or liquid media. Also among these embodiments are those in which the cleaning unit includes at least one removing device, which includes mechanical scrapers in the form of brushes, sealing lips made of a resilient material, or suction elements, in order to remove solid or liquid adhesions from the surface of the hollow body. In such embodiments, it is possible for the removing device to have a mechanical scraper that is drivable in a motor-driven manner. Also among these embodiments are those in which the cleaning unit extends onto or into the hollow body in such a manner that at least solid or liquid adhesions can be removed from an outside surface of the hollow body.

In some embodiments, the hollow body is at least partially closed. Among these are embodiments in which a gas line leads into an interior of the hollow body. These embodiments also include those in which a gas line or opening leads out of the interior of the hollow body.

In another aspect, the invention features a method for inspecting containers by using the foregoing device. Practices of this method include those that include rotating the hollow body; supplying containers; suspended transport in the region of the inspection unit; inspecting the containers; and removing the containers.

Other practices include cleaning a surface of the hollow body, either continuously, or at intervals.

Yet other practices include directing a gas into an interior of the hollow body.

Additional practices include maintaining the interior of the hollow body at a pressure greater than ambient pressure

BRIEF DESCRIPTION OF THE DRAWINGS

These and other features of the invention will be apparent from the following detailed description and the accompanying drawings in which.

Figure 1:
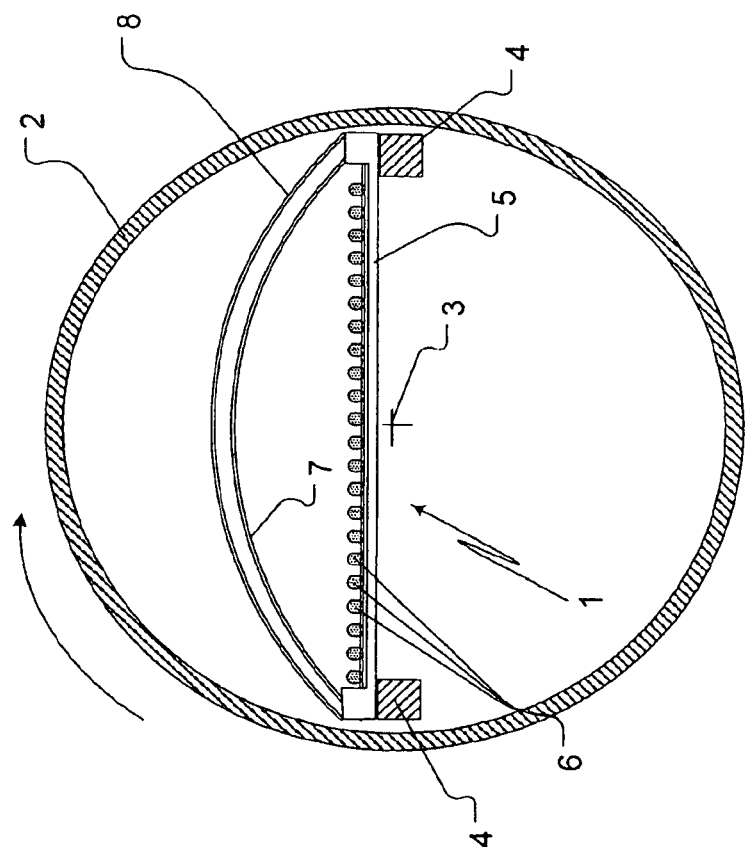
FIG. 1 shows an inspection device.

Reference numerals identify similar structures in all the drawings.

DETAILED DESCRIPTION

FIG. 1 shows a sectional drawing of an illuminating unit 1 of an inspection device. In the example shown, a hollow body is embodied as a transparent tube 2 has a diameter of 130 mm and that is made of an acrylic glass that is transparent to UV light. The tube 2 is mounted so as to be rotatable about an axis 3 emerging from the drawing plane.

Many known solutions are available to one of ordinary skill in the art for the bearing arrangement and the driving means. Consequently, the double bearing arrangement at both ends of the tube 2 and the driving means at one end of the tube selected here are not shown.

The cuboid-shaped illuminating unit 1 rests on two support arms 4 and is located within the interior of the tube 2. The rear suspension of the support arms 4 and of a motor-driven driving means of the transparent tube 2 are not shown in any detail, as one of ordinary skill in the art would be familiar with such devices.

The illuminating unit 1 includes a planar, horizontal support 5 on which is disposed a diode field that includes a plurality of diodes 6 connected electrically to a voltage source in a manner not shown.

Two arc-shaped elements are located above the illuminating unit 1. The bottom arc-shaped element is the diffusion element 7 and the top arc-shaped element is a polarization element 8. The largest distance between the diodes 6 and the diffusion element 7, which is the depth of the dishing, is 40 mm. The diffusion element 7 is spanned by the polarization element 8. The distance between the polarization element 8 and the diffusion element 7 is less than the depth of the dishing. In the illustrated example, the polarization element 8 comprises a linear polarization foil.

Figure 2:
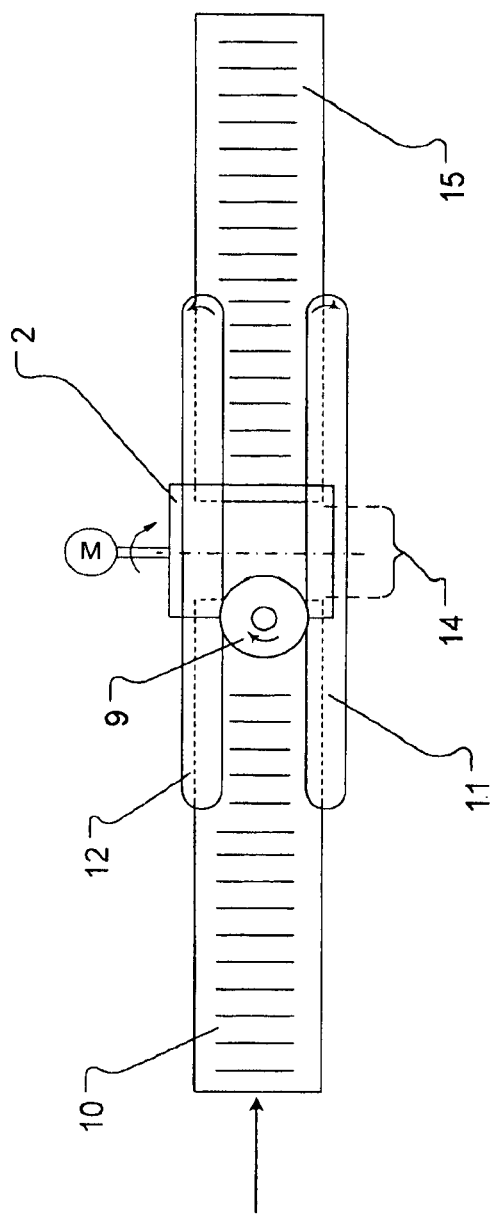
FIG. 2 shows a top view of the device shown in FIG. 1.

FIG. 2 shows a top view of an inspection device that incorporates the illuminating unit 1. A bottle 9 is situated on a supplying conveyor belt 10 that conveys the bottle 9 in the direction of the arrow towards the illuminating unit 1. In the stage of the method shown, the bottle 9 is already situated within an effective range of vertical lifting belts 11 and 12 directly in front of or already partially above a gap 14 that is formed between the supplying conveyor belt 10 and a removing conveyor belt 15. From the viewpoint shown in FIG. 2, the illuminating unit 1 is surrounded by the transparent tube 2 and also covered by the diffusion element 7 and the polarization element 8. Consequently, it cannot be seen in the figure. The transparent tube 2 rotates about the axis 3, which is situated below the gap 14.

In the example shown, the endlessly circulating lifting belts are driven at different speeds such that the bottle 9, when situated within the effective range of the lifting belts 11 and 12, rotates about its central axis.

Figure 3:
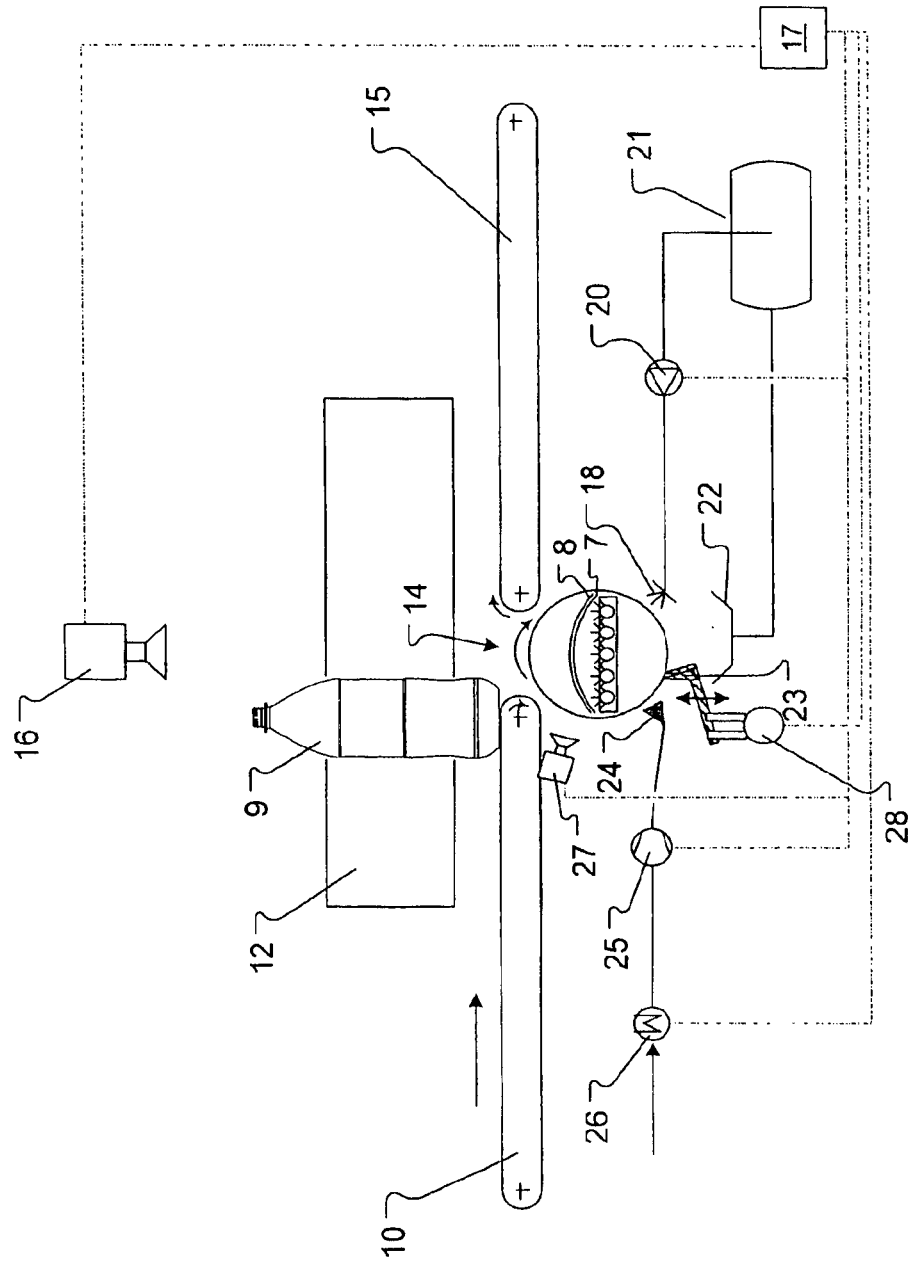
FIG. 3 shows a side view of the device shown in FIG. 1.

FIG. 3 shows the illuminating unit 1 with the rotating, transparent tube 2 located in the gap 14 between the conveyor belts 10 and 15. The illuminating unit 1 is spanned by the polarization element 7 and the diffusion element 8. Two cameras 16 are placed above the gap 14. These cameras 16 receive the signals and forward them to an evaluating-and-control unit 17. A cleaning unit 18 is located below the transparent tube 2 in the region of the gap 14. The cleaning unit 18 includes a spray head 19, a pump 20, a storage container 21, a collecting tray 22, a motor-driven pivotable scraper 23, and a drying unit.

When actuated by the evaluating-and-control unit 17, the pump 20 and the spray head 19 cooperate to sequentially spray the outside surface of the transparent tube 2. Prior to this, or at the same time, the scraper 23, which is driven by the motor 28, is moved to the surface of the transparent tube 2. The scraper 23 has double wiping lips, comparable to a windscreen wiper, and is produced from a silicone material. On account of the arrangement, part of the adhesion flows or drops from the deepest tube portion into the collecting tray 22. The scraper 23 removes the remaining adhesions and moisture and drops them into the collecting tray 22. A pipeline directs cleaning fluid into the storage container 21, where it is available to be used again.

A drying unit located downstream of the scraper 23 in the direction of rotation includes a hot air blower 24 that accomplishes the final drying of the cleaned outside surface of the tube. The evaluation-and-control unit 17 also activates a compressor 25 connected to the hot air blower 24 and an associated heating unit 26.

The surface of the protective tube 2 can consequently be cleaned in an optimum manner. Continuously abradant elements or scrapers, which themselves result in contamination, are avoided. In the present example, the surface of the tube 2 is monitored by a camera 27 that is downstream of both the scraper 23 and the hot air blower 24 in the direction of rotation. This corresponds to monitoring the cleaning performance of the cleaning unit 18. Error messages or deviations from the required value are also forwarded to the evaluation-and-control unit 17, where they are processed.

The invention claimed is:

1. An inspection device for checking containers, said inspection device comprising at least one conveying section or one conveying star for supplying and removing the containers, an illuminating unit, an optical measuring unit and a control unit, wherein the illuminating unit is surrounded by a transparent hollow body that is mounted so as to be rotatable about the central axis, wherein the hollow body is drivable in a motor-driven manner directly or by suitable operative connections, and wherein an axis of rotation of the hollow body is aligned parallel or transversely relative to a conveying direction of the containers.

2. The inspection device according to claim 1, wherein the hollow body comprises a tube produced from a material or a material mixture, the material or material mixture being transparent to rays of wavelengths in the optically-visible range, in the infrared range and/or in the ultraviolet range, and wherein the material or material mixture is at least partially transparent to said rays.

3. The inspection device according to claim 1, further comprising a diffusion element located between the hollow body and a top side of the illuminating unit.

4. The inspection device according to claim 3, wherein the diffusion element is arc-shaped and located between the hollow body and the top side of the illuminating unit.

5. The inspection device according to claim 3, further comprising a polarization filter that is located between the hollow body and a top side of the illuminating unit.

6. The inspection device according to claim 5, wherein the polarization filter is arc-shaped and is located between the hollow body and a top side of the illuminating unit.

7. The inspection device according to claim 5, wherein the polarization filter is located between the hollow body and the diffusion element or the sequence of polarization filter and diffusion element is inverted.

8. The inspection device according to claim 1, further comprising at least one cleaning unit located on the hollow body.

9. The inspection device according to claim 8, wherein the at least one cleaning unit includes at least one feeding device, which includes outlets or nozzles for illuminating an outside surface of the hollow body, wherein the feeding device is suitable for gaseous or liquid media.

10. The inspection device according to claim 8, wherein the at least one cleaning unit includes at least one removing device, which includes mechanical scrapers in the form of brushes, sealing lips made of a resilient material, or suction elements, in order to remove solid or liquid adhesions from the surface of the hollow body.

11. The inspection device according to claim 10, wherein the removing device comprises the at least one mechanical scraper that is drivable in a motor-driven manner.

12. The inspection device according to claim 8, wherein the cleaning unit extends onto or into the hollow body in such a manner that at least solid or liquid adhesions can be removed from an outside surface of the hollow body.

13. The inspection device according to claim 1, wherein the hollow body is at least partially closed.

14. The inspection device according to claim 13, wherein at least one gas line leads into an interior of the hollow body.

15. The inspection device according to claim 14, wherein at least one gas line or opening leads out of the interior of the hollow body.

16. A method for inspecting containers, said method comprising using the inspection device recited claim 1.

17. The inspection method according to claim 16, further comprising: rotating the hollow body; supplying containers; suspending transport in the region of the inspection unit; inspecting the containers; and removing the containers.

18. The inspection method according to claim 16, further comprising, permanently or at intervals, cleaning a surface of the hollow body.

19. The inspection method according to claim 16, further comprising directing a gas into an interior of the hollow body.

20. The inspection method according to claim 19, further comprising maintaining the interior of the hollow body at a pressure greater than ambient pressure.

* * * * *